(12) United States Patent
Nakamoto et al.

(10) Patent No.: US 8,673,287 B2
(45) Date of Patent: Mar. 18, 2014

(54) ANTI-OBESITY COMPOSITION CONTAINING ACACIA BARK DERIVATIVE

(75) Inventors: Yusho Nakamoto, Hatsukaichi (JP); Keiko Ono, Hatsukaichi (JP)

(73) Assignee: Mimozax Co., Ltd., Hatsukaichi-shi (JP)

( * ) Notice: Subject to any disclaimer, the term of this patent is extended or adjusted under 35 U.S.C. 154(b) by 0 days.

(21) Appl. No.: 12/376,939

(22) PCT Filed: Aug. 10, 2006

(86) PCT No.: PCT/JP2006/315864
§ 371 (c)(1),
(2), (4) Date: Feb. 9, 2009

(87) PCT Pub. No.: WO2008/018139
PCT Pub. Date: Feb. 14, 2008

(65) Prior Publication Data
US 2010/0008887 A1     Jan. 14, 2010

(51) Int. Cl.
*A61K 36/48* (2006.01)
*A61K 31/05* (2006.01)
*A61K 31/765* (2006.01)
*A61P 3/04* (2006.01)

(52) U.S. Cl.
USPC ........................ 424/78.38; 424/775; 514/731

(58) Field of Classification Search
None
See application file for complete search history.

(56) References Cited

U.S. PATENT DOCUMENTS

| | | | |
|---|---|---|---|
| 5,629,338 A | 5/1997 | Okuda et al. | |
| 5,968,517 A * | 10/1999 | Duncan et al. | 424/770 |
| 6,290,993 B1 | 9/2001 | Anderson et al. | |
| 6,294,190 B1 | 9/2001 | Nakahara et al. | |
| 6,350,594 B1 * | 2/2002 | Clarke et al. | 435/72 |
| 7,514,469 B2 | 4/2009 | Jia | |
| 2003/0180402 A1 | 9/2003 | Jia et al. | |
| 2003/0216481 A1 * | 11/2003 | Jia | 514/732 |
| 2003/0232099 A1 | 12/2003 | Pan et al. | |
| 2004/0186062 A1 * | 9/2004 | Burnett et al. | 514/27 |
| 2005/0058722 A1 | 3/2005 | Managoli | |
| 2005/0095332 A1 * | 5/2005 | Stanley | 426/481 |
| 2006/0204599 A1 * | 9/2006 | Wheat | 424/757 |
| 2008/0124415 A1 * | 5/2008 | Tanaka et al. | 424/775 |

FOREIGN PATENT DOCUMENTS

| | | |
|---|---|---|
| CN | 1753681 A | 3/2006 |
| FR | 2 710 533 A1 | 4/1995 |
| JP | 64-025726 U | 2/1989 |
| JP | 3-287507 A | 12/1991 |
| JP | 6-065074 A | 3/1994 |
| JP | 7-138178 A | 5/1995 |
| JP | 7-300422 A | 11/1995 |
| JP | 8-259557 A | 10/1996 |
| JP | 9-291039 A | 11/1997 |
| JP | 10025238 A | 1/1998 |
| JP | 11-005975 A | 1/1999 |
| JP | 11-180888 A | 7/1999 |
| JP | 2000-044472 A | 2/2000 |
| JP | 2000-073056 A | 3/2000 |
| JP | 2001-064172 | 3/2001 |
| JP | 2001-098264 A | 4/2001 |
| JP | 2002-010753 A | 1/2002 |
| JP | 2002051735 A | 2/2002 |
| JP | 2002-275076 A | 9/2002 |
| JP | 2003-519092 A | 6/2003 |
| JP | 2003-313138 A | 11/2003 |
| JP | 2003-342185 A | 12/2003 |
| JP | 2004-008215 A | 1/2004 |
| JP | 2004-024054 A | 1/2004 |
| JP | 2004-051513 A | 2/2004 |
| JP | 2004-075579 A | 3/2004 |
| JP | 2004091464 A | 3/2004 |
| JP | 2004-217559 A | 8/2004 |
| JP | 2004-300117 A | 10/2004 |
| JP | 2004532811 T | 10/2004 |
| JP | 2004-323362 A | 11/2004 |
| JP | 2004-352639 A | 12/2004 |
| JP | 2004352639 A | 12/2004 |
| JP | 2005-068081 | 3/2005 |
| JP | 2005-521715 A | 7/2005 |
| JP | 2005-239559 A | 9/2005 |
| JP | 2005-529898 A | 10/2005 |
| JP | 2006-232781 A | 9/2006 |
| JP | 2006-232782 A | 9/2006 |
| WO | WO 03/082312 A1 | 10/2003 |
| WO | WO-03/092599 A2 | 11/2003 |
| WO | WO 2005-020932 A2 | 3/2005 |
| WO | WO2006/003909 * | 6/2005 |

OTHER PUBLICATIONS

Ishada et al. Solid Sampling Technique for Direct Detection of Condensed tannins in Bark by Matrix-Assisted Laser Desorption/ionization Mass Spectrometry. http://www.ran.nagoya-u.ac.jp/energy/papers/RCM706.pdf.*

Jacobus et al., Condensed Tannins: Direct Synthesis, Structure and Absolute Configuration of Four Biflavonoids from Black Wattle (Acacia mearnsii) Bark, J.C.> Chem. Comm. 1978. http://pubs.rsc.org/en/content/articlepdf/1978/c3/c39780000700.*

Johns et al. Maasai Gummivory: Implications for Paleolithic Diets and Contemporary Health. vol. 41, No. 3, Jun. 2000.*

Duan et al. Condensed Tannins From Steamed *Acacia mearnsii* bark, Jul. 2005. Retreived online at : http://www.degruyter.com/dg/viewarticle/j$002fhfsg.2005.59.issue-3$002fhf.2005.048$002fhf.2005.048.xml.*

Burnett et al. A Medicinal Extract of *Scutellaria baicalensis* and *Acacia catechu* Acts as a Dual Inhibitor of Cyclooxygenase and 5-Lipoxygenase to Reduce Inflammation. J Med Food 10(3) 2007. Retreived online at: http://www.cararthron.com.au/studies/Medicinal%20Extract%20of%20Scutellaria.pdf.*

(Continued)

*Primary Examiner* — Scott Long
*Assistant Examiner* — Sarah Alawadi
(74) *Attorney, Agent, or Firm* — Birch, Stewart, Kolasch & Birch, LLP

(57) ABSTRACT

It is intended to provide a composition having an excellent anti-obesity action without potential for adverse side effects and the like even if taken for a long period of time. The composition is an anti-obesity composition containing an *acacia* bark derivative.

6 Claims, No Drawings

(56) References Cited

OTHER PUBLICATIONS

African Territories Wattle Industry Fund Limited, Properties, Composition, Reactions and Industrial Applications of Mimosa Extract, Jan. 1980. pp. 2-10.

Byers, "What can randomized controlled trials tell us about nutrition and cancer prevention?" CA Cancer J Clin, Nov.-Dec. 1999, vol. 49, No. 6, pp. 353-361.

Chang et al., "Antioxidant activity of extracts from *Acacia confusa* bark and heartwood," J Agric Food Chem, Jul. 2001, vol. 49, No. 7, pp. 3420-3424.

Cheng et al., "A novel approach to microcalcification detection using fuzzy logic technique," IEEE Trans Med Imaging, Jun. 1998, vol. 17, No. 3, pp. 442-450.

De Oliveira et al., "Antitumor Activity of Condensed Flavanols," An. Acad. Brasil Cleric vol. 44, pp. 41-44, Academia Brasileira de Ciencias (1972).

Duan et al., "Condensed tannins from steamed *Acacia mearnsii* bark," Holzforschung, May 2005, vol. 59, No. 3, pp. 289-294.

Fragrance Journal, 1995, 23(10), pp. 96-102 (with English language abstract).

Garewal et al., "Clinical experience with the micronucleus assay," J Cell Biochem Suppl, 1993, vol. 52, No. 17F, pp. 206-212.

Granziero et al., "Adoptive immunotherapy prevents prostate cancer in a transgenic animal model," Eur J Immunol, Apr. 1999, vol. 29, No. 4, pp. 1127-1138.

Haridas et al., "Avicins: triterpenoid saponins from *Acacia victoriae* (Bentham) induce apoptosis by mitochondrial perturbation," PNAS, May 8, 2001, vol. 98, No. 10, pp. 5821-5826.

http://www.merck.com/mmhe/sec15/ch180/ch180c.html, downloaded Apr. 14, 2009, "Risk Factors for Cancer," last review/revision Aug. 2008 by Bruce A. Chabner, MD; Elizabeth Chabner Thompson, MD, MPH.

http://www.merckmanuals.com/home/sec15/ch180/ch180a. html?qt=cancer&alt=sh, downloaded Dec. 4, 2010, "Overview of Cancer: Merck Manual Home Edition," last full review/revision Aug. 2008 by Bruce A. Chabner, MD; Elizabeth Chabner Thompson, MD, MPH.

Japanese Office Action issued in Japanese Patent Application No. 2005-132746 on Aug. 2, 2011.

Japanese Office Action issued in JP 2005-132745 on Sep. 13, 2011, with English translation.

Kaur, "Antimutagenicity of ether and ethyl acetate fractionsn of *Acacia nilotica* in Ames assay", Breast, vol. 12, No. Supplement, (2003) p. s47.

Kronborg O., "Population screening for colorectal cancer, the goals and means," Ann Med, Oct. 1991, vol. 23, No. 4, pp. 373-379.

Liu et al., "Antidiabetic effect of Pycnogenol French maritime pine bark extract in patients with diabetes type II," Life Sci, Oct. 8, 2004, vol. 75, No. 21, pp. 2505-2513.

Ohara "Chemical Properties and Application Development of Bark Tannin", APAST, vol. 13, No. 1 (Jan. 2003) pp. 7-11 (and English Translation, pp. 1-10).

Ohara et al., "Condensed Tannins from *Acacia mearnsii* and Their Biological Activities." Mokuzai Gakkaishi, 1994, vol. 40, No. 12, pp. 1363-1374.

Orwa et al., "*Acacia mearnsii*, black wattle", Agroforestry Database 4.0 (2009) pp. 1-5.

Prakash et al., "Characterisation of Tannin from Indian Wattle (*Acacia mearnsii*) Bark," Indian Journal of Forestry, 1991, vol. 14, No. 4, pp. 299-302.

Properties, Composition, Reactions and Industrial Applications of Mimosa Extract, African Territories Wattle Industry Fund Limited, Jan. 1980, London, England.

Roux, "The Biogenesis of Bark and Heartwood Tannins of Some *Acacia* spp. and Their Taxonomic Significance," South African Journal of Science, 1962, vol. 58, No. 12, pp. 389-392.

Seigler, "Phytochemistry of *Acacia-sensu* lato," Biochemical Systematics and Ecology, 2003, vol. 31, No. 8, pp. 845-873.

Seiji Ohara, "Juhi Tannin no Kagaku Tokusei to Yoto Kaihatsu." APAST, 2003, vol. 13, No. 1, pp. 7-11.

Taguchi et al., "Evaluation of antipruritic effect of apple polyphenols using a new animal model of pruritus." J. Tokyo Med. Univ., Feb. 15, 2002, vol. 60, No. 2, pp. 123-129.

Takagi et al., "Tyrosinase inhibitory activity of proanthocyanidins from woody plants." J. Wood Sci., 2003, vol. 49, No. 5, pp. 461-465.

Tomatis, "Environmental cancer risk factors. A review." Acta Oncol, 1988, vol. 27, No. 5, pp. 465-472.

U.S. Office Action issued in U.S. Appl. No. 12/376,905 on Dec. 20, 2010.

U.S. Office Action issued in U.S. Appl. No. 12/376,905 on Jan. 3, 2011.

U.S. Office Action issued in U.S. Appl. No. 12/376,895 on Jan. 6, 2011.

U.S. Office Action issued in U.S. Appl. No. 12/376,895 on May 2, 2011.

U.S. Office Action issued in U.S. Appl. No. 12/376,895 on Nov. 2, 2010.

U.S. Office Action issued in U.S. Appl. No. 12/376,902 on Jan. 3, 2011.

U.S. Office Action issued in U.S. Appl. No. 12/376,902 on Jun. 15, 2011.

U.S. Office Action issued in U.S. Appl. No. 12/376,902 on Oct. 20, 2010.

U.S. Office Action issued in U.S. Appl. No. 12/376,904 on Aug. 31, 2010.

U.S. Office Action issued in U.S. Appl. No. 12/376,904 on Feb. 16, 2011.

U.S. Office Action issued in U.S. Appl. No. 12/376,904 on Jun. 17, 2011.

U.S. Office Action issued in U.S. Appl. No. 12/376,905 on Jun. 15, 2011.

Wassel et al., "Phytochemical examination and biological studies of *Acacia nilotica* L. Willd and *Acacia farnesiana* L. Willd growing in Egypt," Egyptian Journal of Pharmaceutical Sciences, 1992, vol. 33, Nos. 1-2, pp. 327-340.

Extended European Search Report issued Feb. 17, 2012, in European Patent Application No. 06782650.3.

Yao et al., "The potential of wattle tannin extracts for fine use," Natural Product Research (Mar. 2006), vol. 20, No. 3, pp. 271-278.

\* cited by examiner

ANTI-OBESITY COMPOSITION CONTAINING ACACIA BARK DERIVATIVE

TECHNICAL FIELD

The present invention relates to an anti-obesity composition derived from a tree belonging to the genus *Acacia*, and to uses as a food, an animal feed material, a medicine and a quasi-drug containing this anti-obesity composition.

BACKGROUND ART

In general, obesity refers to a condition of excess accumulation of fatty tissue in the body. Body mass index (BMI), which is adopted in a health check up, etc., is determined by dividing body weight (kg) by the square of height (m). Body weight for which BMI is 22 is referred to as standard body weight, and a body weight that is 10% or more higher than the standard body weight is referred to as being overweight, while a body weight that is 20% or more higher than the standard body weight is referred to as obesity. The number of obese persons and persons who would become obese has increased in recent years due to Westernization of the diet, a lack of exercise resulting from the development of transportation facilities and the like. In particular, obesity is closely correlated with the onset of diseases such as hypertension, diabetes, fatty liver, arteriosclerosis, stroke, hyperlipemia, peripheral circulatory disorders and ischemic heart disease, and the prevention or decrease of obesity is extremely important from the viewpoint of preventing and treating the onset of these diseases.

Although improvement of lifestyle in terms of diet therapy and exercise therapy is desirable for preventing or decreasing obesity, this cannot always be easily achieved. In addition, although drug therapy is available for the treatment of obesity, including the use of lipid absorption inhibitors and intestinal absorption inhibitors, their use is limited to cases of serious obesity.

Amidst these circumstances, various products using natural ingredients having various actions and having less potential for adverse side effects and the like even if taken for a long period have been sold commercially in the form of a diet food and the like for the purpose of preventing or decreasing obesity, and searches are being made for novel substances having an anti-obesity activity.

For example, Patent Document 1 discloses that a dried powder, extract or purified product of Kouki leaves or bark has a weight loss effect on rats and humans. In addition, Patent Document 2 discloses that tannin, a kind of polyphenol has α-amylase inhibitory effects and anti-obesity effects.

On the other hand, with respect to *acacia acacia* honey is known, and tannin which is extracted from bark thereof is known to be able to be used as a tanning agent or a wood adhesive, while more recently, extracts of genus *Acacia* have been disclosed to have selective inhibitory effects on COX-2 (Patent Document 3), and bark of genus *Acacia* has been disclosed to have active oxygen eliminating effects (Patent Document 4) and skin whitening effects due to the effect of inhibiting tyrosinase activity (Patent Document 5). However, *acacia* bark and polyphenols derived from *acacia* bark have heretofore not been known to have an anti-obesity action.

[Patent Document 1] JP2004-091464A
[Patent Document 2] JP2002-051735A
[Patent Document 3] JP2004-532811A
[Patent Document 4] JP2004-352639A
[Patent Document 5] JP10-025238A

DISCLOSURE OF THE INVENTION

Problems to be Solved by the Invention

An object of the present invention is to provide a composition having an excellent anti-obesity action without potential for adverse side effects and the like even if taken for a long period of time.

Means for Solving the Problems

As a result of conducting extensive studies to solve the above problems, the inventors of the present invention found that an *acacia* bark derivative has an anti-obesity action to be useful for the prevention, decrease or treatment of obesity, thereby leading to the completion of the present invention.

Namely, the present invention relates to an anti-obesity composition containing an *acacia* bark derivative(s).

In addition, the present invention also relates to a method for preventing or treating obesity using an *acacia* bark derivative(s).

Moreover, the present invention relates to a method for using an *acacia* bark derivative(s) for producing a composition for preventing or treating obesity.

Effects of the Invention

According to the present invention, a composition having an anti-obesity action can be provided.

Moreover, according to the present invention, a composition is provided which is safe and has less potential for adverse side effects and the like even if taken for a long period of time.

BEST MODE FOR CARRYING OUT THE INVENTION

There are no particular limitations on the *acacia* bark derivative able to be used in the present invention provided that it is obtained by using as a raw material bark of a tree belonging to the genus *Acacia* (the tree is referred to as "*acacia*" or "genus *Acacia*" hereinafter), examples of which derivatives include a strip and a powder of *acacia* bark, and a suspension thereof, an extract such as a liquid extract, a concentrated liquid extract and a powdered extract of *acacia* bark, and a purified product obtained by purifying these extracts. The extract of *acacia* bark and particularly *acacia* bark polyphenols are preferable for production of excellent anti-obesity activity.

In the present invention, only a single form of these *acacia* bark derivatives may be used, or alternatively two or more forms thereof may be used in combination.

Although there are no particular limitations on *acacia* able to be used in the present invention so long as it is a tree belonging to the genus *Acacia*, with respect to obtaining an *acacia* bark derivative having an excellent anti-obesity action, bark of the genus *Acacia* selected from the group consisting of scientific name: *Acacia* mearnsii De Wild. (generic name: black wattle), scientific name: *Acacia* mangium Willd. (generic name: *acacia* mangium), scientific name: *Acacia* dealbata Link, scientific name: *Acacia* decurrens Willd. and scientific name: *Acacia* pycnantha Benth. are preferable, while *Acacia* mearnsii De Wild. and *Acacia* mangium Willd. are particularly preferable.

In the present invention, only a single type of these *acacia* bark may be used, or alternatively two or more forms thereof may be used in combination.

The aforementioned *acacia* bark can normally be obtained by cutting down an *acacia* tree, pealing off only bark and then drying the bark more preferably by sun-drying.

Bark of *acacia* is comprised of an outer bark and a somewhat fibrous inner bark, and when dried to a moisture content of about 20% or less, can be easily finely pulverized with a size reduction mill such as a hammer mill. In the present invention, both the outer bark and inner bark of the genus *Acacia* may be used together or either one may be used alone as the *acacia* bark.

The aforementioned strip of *acacia* bark can be obtained in accordance with commonly used methods by pulverizing the *acacia* bark to a suitable size.

In addition, although the aforementioned powder of *acacia* bark can be obtained by pulverizing the *acacia* bark into a powder in accordance with commonly used methods, in particular, the particle diameter of the resulting powder is preferably 100 μm or less and particularly preferably 50 to 70 μm. Powder fractionation can be carried out by pulverizing the bark dried to a moisture content of 20% or less to a suitable size such as a particle diameter of about 1.6 mm or less, and then classifying the resulting powder with a vibrating screen or the like to obtain the required powder.

The aforementioned extract of *acacia* bark can be obtained by extraction from the *acacia* bark in accordance with commonly used methods. In order to obtain an extract of *acacia* bark having an excellent anti-obesity action, it is preferably extracted from the *acacia* bark with an alcohol or a polar solvent.

Ethanol, etc. can be used as the alcohol, and water, etc. can be used as the polar solvent, and these solvents may be used singly or in combination of two or more kinds as necessary. A mixed solvent of water and the alcohol such as ethyl alcohol is particularly preferable for production of an excellent anti-obesity action.

Moreover, the extraction procedure may be carried out a number of times using the same or different solvents.

In terms of obtaining an extract having an excellent anti-obesity action, an extract which is obtained from the *acacia* bark by extraction with water or hot water, and then further extraction from the resulting extract with ethanol may be used.

Although the extraction is carried out by adding the solvent to a strip, a powder or the like of the *acacia* bark followed by stirring as necessary, there are no particular limitations on temperature, time or solid-liquid ratio. In the case of using water as the solvent, the extraction may also be carried out with hot water. The resulting liquid extract may be freeze-dried or spray-dried directly, or may be freeze-dried or spray-dried after concentrating under reduced pressure. The resulting extract can be in various forms, such as a liquid extract, solution, powder, concentrate or paste, and can be used in a wide range of forms as necessary.

Moreover, the *acacia* bark extract of the present invention obtained in any of these forms can be used directly as a anti-obesity composition, or a purified product obtained by purifying the extract as necessary can also be used as a anti-obesity ingredient.

In the present invention, ingredients contained in bark of the genus *Acacia* are also examples of the *acacia* bark derivatives. Examples of such ingredients are the *acacia* hark polyphenols. The *acacia* bark polyphenols are particularly preferable ingredients since they produce excellent anti-obesity action.

The *acacia* bark polyphenols of the present invention refer to a type of condensed tannins in the form of polymers in which flavanols having as a basic skeleton flavan-3-ol such as (−)-fisetinidol, (−)-robinetinidol, (+)-catechin and (+)-gallocatechin are linked by C4-C8 or C4-C6 bonds. Here, the molecular weights of such condensed tannins are preferably 300 to 3000 and particularly preferably 500 to 3000. The *acacia* bark polyphenols used in the present invention can be obtained from the powder, etc. of the *acacia* bark by extracting with hot water as previously described.

In addition, examples of commercially available *acacia* bark polyphenols include MIMOSA ME POWDER, MIMOSA MS POWDER, MIMOSA GS POWDER, MIMOSA FS POWDER, MIMOSA WS POWDER, MIMOSA RG POWDER, MIMOSA RN POWDER, MIMOSA DK POWDER, MIMOSA AL POWDER, MIMOSA CR POWDER and GOLDEN MIMOSA POWDER (all registered trademarks) which are manufactured by Mimosa Central Co-operative Ltd., and the like.

An anti-obesity action as referred to in the present invention refers to action that reduces or suppresses body weight or the amount, weight or concentration of body fat by ingesting a certain substance into the body as compared with not ingesting that substance.

Body fat as used in the present invention includes subcutaneous fat and visceral fat formed due to the accumulation of fat in fat cells, as well as cholesterol, neutral fats (triglycerides), phospholipids and free fatty acids present in the blood.

Although the composition of the present invention may be the *acacia* bark derivative(s) such as the *acacia* bark, the extract(s) thereof, the purified product(s) thereof or the *acacia* bark polyphenol(s) per se, it may also contain other substance(s) having an anti-obesity action, such as flavonoid(s) contained in a plantain.

Although the composition of the present invention may be the *acacia* bark, the extract(s) thereof, the purified product(s) thereof or the *acacia* bark polyphenol(s) per se, it may contain vehicles, sweeteners, sour flavorings, thickeners, fragrances, pigments, emulsifiers, and other materials which are ordinarily used in foods, so long as they do not undermine the effects of the present invention.

The composition according to the present invention can be used as a food or an animal feed material, for example, as a health food, a functional food, a health supplement food, a food for specified health use, a beauty food or a nutritional supplement food (supplement) for purposes such as preventing or decreasing obesity. For example, these foods or animal feed material may also be in the form of a beverage such as tea or juice; ice cream, jelly, candy, chocolate or chewing gum, etc. In addition, they may also be in the form of liquids, powders, granules, capsules or tablets. Here, animals fed by the animal feed material include all animals requiring the prevention, decrease or treatment of obesity, including pets, livestock or animals bred at zoos, etc.

In addition, the composition according to the present invention can be used as a medicine or a quasi-drug for the prevention, decrease, treatment or the like of obesity. These medicines and drugs can be administered, for example, orally in the form of tablets, coated tablets, sugar coated pills, hard or soft gelatin capsules, liquids, emulsions or suspensions.

There are no particular limitations on an ingested amount of the composition according to the present invention, and the ingested amount can be suitably selected depending on the dosage form as well as the age, body weight and symptoms of an ingesting person such as a user or patient, or an ingesting animal. For example, it is desired that the ingesting person or ingesting animal orally ingests an amount of the *acacia* bark polyphenol(s) ranging from 0.001 to 1 g, preferably from 0.001 to 0.5 g and more preferably from 0.005 to 0.1 g per 1 kg of body weight per day in terms of the amount of active ingredient, since it produces an excellent anti-obesity action.

The duration of ingestion can be arbitrarily determined depending on the age and symptoms of the user or patient.

Although the following provides a more detailed explanation of the present invention through examples thereof, the present invention is not limited thereto.

EXAMPLES

Although the following provides a more detailed explanation of the present invention through production examples, test examples and formulation examples thereof, the present invention is not limited thereto. In particular, although the following examples are indicated without making a distinction between the outer bark and inner bark of the *acacia* bark of the present invention, the outer bark can be separated from the inner bark and each can also be used, separately.

In the following production examples, test examples and the like, each *acacia* of the present invention is indicated with numbers shown in parentheses after each scientific name. For example, *acacia* known by the scientific name of *Acacia mearnsii* De wild. is indicated as *Acacia* No. 1.

Scientific name: *Acacia mearnsii* De Wild. (No. 1), scientific name: *Acacia mangium* Willd. (No. 2), scientific name: *Acacia dealbata* Link (No. 3), scientific name: *Acacia decurrens* Willd. (No. 4), scientific name: *Acacia pycnantha* Benth. (No. 5).

In addition, percentages (%) refer to percent by weight (wt %) unless specifically indicated otherwise.

Production Example 1

*Acacia* Bark Powder

Bark of *Acacia* No. 1 was dried to a moisture content of 20% or less and after pulverizing the dried bark in a hammer mill to a powder having a particle diameter of 1.6 mm or less (the powder passing through a 10 mesh Tyler screen), the powder was further classified with a vibrating screen to obtain a fine powder having a particle diameter of 63 μm or less (passing through a 250 mesh screen).

Fine powders each having a particle diameter of 63 μm or less were similarly obtained by pulverizing bark of the remaining four types of *acacia* namely *Acacia* No. 2 to *Acacia* No. 5. Although there were some differences in the efficiency by which the fine powder passed through the 250 mesh screen depending on the type, all of the target fine powders were able to be obtained.

Production Example 2

*Acacia* Bark Extract

Bark of each *Acacia* No. 1 to 5 of the present invention was dried to a moisture content of 20% or less and after pulverizing the dried bark in a hammer mill to a powder having a particle diameter of 1.6 mm or less, five times the amount of hot water were added to 100 g of the dried pulverized bark followed by extraction for 15 minutes after boiling, and then filtering using a 10 to 20 μm filter. The resulting filtrate was spray-dried in a spray dryer to obtain 40 g of each bark extract.

The bark extracts are hereinafter indicated as *Acacia* Hot Water Extracts Nos. 1 to 5, respectively.

Production Example 3

*Acacia* Bark Extract

*Acacia* bark of the present invention was dried to a moisture content of 20% or less and after pulverizing the dried bark in a hammer mill to a powder having a particle diameter of 1.6 mm or less, five times the amount of ethanol were added to 100 g of the dried pulverized bark followed by extraction for 15 minutes while refluxing after boiling, and then filtering using a 10 to 20 μm filter. After evaporating the ethanol from the resulting filtrate, the concentrate was spray-dried in a closed spray dryer to obtain 40 g of bark extract (to be indicated hereinafter in the manner of *Acacia* Ethanol Extract No. 1).

*Acacia* Ethanol Extracts Nos. 1 to 5 were obtained in the same manner.

Production Example 4

*Acacia* Bark Extract

Three times the amount of ethanol were added to 10 g of the *acacia* hot water extract obtained in Production Example 2 followed by extraction for 15 minutes while refluxing after boiling, and then filtering using a 10 to 20 μm filter. The ethanol was evaporated from the resulting filtrate, water was added thereto, and then freeze-dried to obtain 9 g of extract (to be indicated hereinafter in the manner of *Acacia* Hot Water Extract Ethanol Fraction No. 1).

*Acacia* Hot Water Extract Ethanol fractions Nos. 1 to 5 were obtained in the same manner.

Test Example 1

Anti-Obesity Test Using Rat High-Fat Diet Loading Model

1. Test Method

Feed containing 5% of *Acacia* Hot Water Extract No. 1 described in Production Example 2 and 20% of lard was fed to rats (Slc:SD, males, age 5 weeks) for 56 days. A control group was given feed mixed with 20% lard.

Weekly water and food consumption were measured once a week followed by calculating the amounts consumed per day.

Triglyceride levels and other blood biochemical values were measured on the day following the final day of dosing using an automated analyzer (Model 7170, Hitachi Instrument Engineering Co., Ltd.). The rats were not fed on the day before. In addition, all visceral fat was excised from the abdominal cavity followed by measuring the absolute weight thereof while also calculating the relative weight (per 100 g of body weight).

Each of the resulting measured values was expressed as the mean±standard error. Testing for the presence of a significant difference from the control group was carried out using the Student's t-test in the presence of a uniform distribution as determined with the F test, or carried out using the Aspin-Welch t-test in the absence of a uniform distribution as determined with the F test. The level of significance was indicated as 5% or 1%.

2. Test Results

The results are shown in the following Tables 1 to 4, None of the rats died or demonstrated abnormalities in general condition.

TABLE 1

Body Weight (g)

| Dose group | No. of animals | Before dosing | Week 1 | Week 2 | Week 3 | Week 4 | Week 5 | Week 6 | Week 7 | Week 8 |
|---|---|---|---|---|---|---|---|---|---|---|
| Control group | 7 | 136 ± 5 | 205 ± 6 | 271 ± 7 | 326 ± 8 | 373 ± 9 | 418 ± 10 | 456 ± 12 | 493 ± 13 | 529 ± 13 |
| Acacia Hot Water Extract No. 1 | 7 | 137 ± 5 | 169 ± 5** | 218 ± 9** | 249 ± 9** | 300 ± 9** | 351 ± 14** | 387 ± 17** | 419 ± 19** | 452 ± 20** |

**$p < 0.01$

TABLE 2

Food Consumption (g/day)

| Dose group | No. of animals | Week 1 | Week 2 | Week 3 | Week 4 | Week 5 | Week 6 | Week 7 | Week 8 |
|---|---|---|---|---|---|---|---|---|---|
| Control group | 7 | 22.0 ± 0.7 | 22.7 ± 0.4 | 23.0 ± 0.4 | 23.2 ± 0.5 | 25.1 ± 0.5 | 23.4 ± 0.8 | 24.5 ± 0.7 | 23.8 ± 0.5 |
| Acacia Hot Water Extract No. 1 | 7 | 17.4 ± 0.5** | 23.8 ± 1.0 | 21.7 ± 0.7 | 24.0 ± 1.0 | 25.4 ± 1.7 | 23.4 ± 1.7 | 22.8 ± 1.5 | 23.4 ± 1.3 |

**$p < 0.01$

TABLE 3

Water Consumption (mL/day)

| Dose group | No. of animals | Week 1 | Week 2 | Week 3 | Week 4 | Week 5 | Week 6 | Week 7 | Week 8 |
|---|---|---|---|---|---|---|---|---|---|
| Control group | 7 | 21.1 ± 1.3 | 22.1 ± 1.5 | 23.3 ± 1.0 | 22.8 ± 1.4 | 25.2 ± 1.8 | 26.5 ± 2.1 | 27.5 ± 2.1 | 29.5 ± 2.8 |
| Acacia Hot Water Extract No. 1 | 7 | 20.3 ± 0.8 | 23.6 ± 1.2 | 23.9 ± 1.3 | 26.6 ± 1.6 | 27.3 ± 2.4 | 26.9 ± 2.1 | 26.9 ± 1.9 | 27.5 ± 1.8 |

TABLE 4

Visceral Fat Weight and Blood Biochemistry Tests

| Dose group | No. of animals | Visceral fat weight g | Visceral fat weight g/100 g | T-CHO mg/dL | TG mg/dL | Phospholipids mg/dL | Free fatty acids µEq/L | Ketones µmol/L |
|---|---|---|---|---|---|---|---|---|
| Control group | 7 | 46.5 ± 3.8 | 9.2 ± 0.6 | 56 ± 6 | 70 ± 10 | 103 ± 6 | 446 ± 95 | 1399 ± 104 |
| Acacia Hot Water Extract No. 1 | 7 | 24.1 ± 3.6** | 5.5 ± 0.6** | 49 ± 1 | 37 ± 5* | 88 ± 2* | 324 ± 30 | 1217 ± 221 |

*$p < 0.05$
**$p < 0.01$

Visceral fat weights, triglyceride levels, phospholipid levels and body weights in the Acacia Hot Water Extract No. 1 dose group decreased in comparison with the control group.

Since there were no differences observed for food consumption and water consumption, the above decreases were thought to be attributable to the administration of Acacia Hot Water Extract No. 1.

On the basis of these results, body fat decreased significantly as a result of the administration of the acacia bark extract.

Test Example 2

Body Fat Reduction Test Using Rat High-Fat Diet Loading Model

1. Test Method

Mixed feed respectively containing 0.5%, 1.5% and 5.0% of Acacia Hot Water Extract No. 1 (Each feed contained 20% of lard) was fed for 56 days to rats (Slc:SD, males, age 5 weeks). A control group was given feed mixed with 20% of lard.

Each parameter was measured in the same manner as in Test Example 1.

The resulting measured values were expressed as the mean±standard error. Testing for the presence of a significant difference between the control group and the *Acacia* Hot Water Extract No. 1 dose groups was carried out using Dunnett's multiple comparison test. The level of significance was indicated as 5% or 1%.

2. Test Results

The results are shown in the following Tables 5 to 8, None of the rats died or demonstrated abnormalities in general condition.

TABLE 5

Body Weight (g)

| Dose group | No. of animals | Before dosing | Week 1 | Week 2 | Week 3 | Week 4 | Week 5 | Week 6 | Week 7 | Week 8 |
|---|---|---|---|---|---|---|---|---|---|---|
| Control group | 10 | 142 ± 7 | 204 ± 13 | 261 ± 18 | 313 ± 23 | 358 ± 26 | 400 ± 23 | 437 ± 24 | 468 ± 25 | 495 ± 25 |
| *Acacia* Hot Water Extract No. 1 0.5% dose group | 10 | 140 ± 7 | 199 ± 13 | 257 ± 18 | 310 ± 23 | 354 ± 27 | 394 ± 27 | 422 ± 34 | 465 ± 38 | 492 ± 37 |
| *Acacia* Hot Water Extract No. 1 1.5% dose group | 10 | 141 ± 6 | 194 ± 12 | 252 ± 20 | 298 ± 26 | 340 ± 35 | 379 ± 35 | 412 ± 37 | 438 ± 38 | 464 ± 45 |
| *Acacia* Hot Water Extract No. 1 5.0% dose group | 10 | 142 ± 8 | 168 ± 7** | 210 ± 14** | 251 ± 19** | 287 ± 24** | 325 ± 24** | 357 ± 25** | 383 ± 24** | 408 ± 24** |

**P < 0.01; significant difference versus value of control group (Dunnett's multiple comparison)

TABLE 6

Food Consumption (g/day)

| Dose group | No. of animals | Week 1 | Week 2 | Week 3 | Week 4 | Week 5 | Week 6 | Week 7 | Week 8 |
|---|---|---|---|---|---|---|---|---|---|
| Control group | 10 | 21.1 ± 1.7 | 22.0 ± 1.8 | 25.2 ± 2.8 | 20.4 ± 2.1 | 22.6 ± 2.3 | 22.0 ± 2.0 | 21.7 ± 2.2 | 21.4 ± 1.7 |
| *Acacia* Hot Water Extract No. 1 0.5% dose group | 10 | 21.5 ± 2.8 | 22.7 ± 1.4 | 24.8 ± 3.5 | 21.2 ± 2.6 | 22.3 ± 2.8 | 22.9 ± 1.7 | 22.5 ± 2.7 | 21.9 ± 2.8 |
| *Acacia* Hot Water Extract No. 1 1.5% dose group | 10 | 22.6 ± 3.0 | 26.6 ± 5.9* | 27.3 ± 4.3 | 22.6 ± 2.5 | 24.0 ± 2.6 | 24.9 ± 4.4 | 25.1 ± 5.3 | 25.0 ± 4.3 |
| *Acacia* Hot Water Extract No. 1 5.0% dose group | 10 | 19.7 ± 2.8 | 26.7 ± 4.9* | 27.5 ± 3.6 | 23.4 ± 4.0 | 26.2 ± 2.8** | 24.5 ± 3.3 | 24.6 ± 3.9 | 27.0 ± 4.5** |

*P < 0.05,
**P < 0.01; significant difference versus value of control group (Dunnett's multiple comparison)

TABLE 7

Water Consumption (mg/day)

| Dose group | No. of animals | Week 1 | Week 2 | Week 3 | Week 4 | Week 5 | Week 6 | Week 7 | Week 8 |
|---|---|---|---|---|---|---|---|---|---|
| Control group | 10 | 21.0 ± 2.4 | 22.6 ± 3.4 | 24.0 ± 4.2 | 23.9 ± 6.1 | 25.1 ± 7.2 | 24.8 ± 4.3 | 25.0 ± 4.9 | 26.5 ± 7.6 |
| *Acacia* Hot Water Extract No. 1 0.5% dose group | 10 | 20.3 ± 2.6 | 22.2 ± 3.2 | 23.7 ± 3.7 | 26.0 ± 6.9 | 26.4 ± 5.7 | 28.5 ± 6.0 | 30.8 ± 8.8 | 30.6 ± 11.1 |
| *Acacia* Hot Water Extract No. 1 1.5% dose group | 10 | 21.5 ± 2.6 | 23.6 ± 3.3 | 23.8 ± 3.8 | 24.0 ± 4.0 | 24.1 ± 3.7 | 24.7 ± 3.7 | 27.2 ± 7.9 | 24.9 ± 4.6 |
| *Acacia* Hot Water Extract No. 1 5.0% dose group | 10 | 20.3 ± 4.2 | 22.5 ± 2.8 | 24.4 ± 5.7 | 24.1 ± 3.6 | 25.4 ± 4.1 | 24.0 ± 3.7 | 23.2 ± 3.0 | 22.5 ± 2.9 |

TABLE 8

Visceral Fat Weight and Blood Biochemistry Tests

| Dose group | No. of animals | Visceral fat weight | | T-CHO mg/dL | TG mg/dL | Phospholipids mg/dL | Free fatty acids μEq/L | Ketones μmol/L |
| --- | --- | --- | --- | --- | --- | --- | --- | --- |
| | | g | g/body weight 100 g | | | | | |
| Control group | 10 | 38.6 ± 8.8 | 8.0 ± 1.6 | 66.0 ± 12.0 | 74.0 ± 21.0 | 111.0 ± 13.0 | 661.0 ± 54.0 | 1094 ± 537 |
| *Acacia* Hot Water Extract No. 1 0.5% dose group | 10 | 36.7 ± 7.4 | 7.7 ± 1.1 | 53.0 ± 17.0 | 74.0 ± 21.0 | 101.0 ± 11.0 | 704.0 ± 104.0 | 1094 ± 307 |
| *Acacia* Hot Water Extract No. 1 1.5% dose group | 10 | 29.6 ± 8.9* | 6.5 ± 1.4* | 53.0 ± 7.0* | 62.0 ± 14.0 | 94.0 ± 8.0** | 620.0 ± 124.0 | 1535 ± 273 |
| *Acacia* Hot Water Extract No. 1 5.0% dose group | 10 | 19.5 ± 6.3** | 4.9 ± 1.4** | 55.0 ± 9.0 | 39.0 ± 14.0** | 89.0 ± 9.0** | 604.0 ± 148.0 | 1801 ± 418** |

*$P < 0.05$,
**$P < 0.01$; significant difference versus value of control group (Dunnett's multiple comparison)

Triglyceride levels and phospholipid levels decreased significantly in the extract dose groups and absorption of fat was suppressed. Since ketone levels increased in the *Acacia* Hot Water Extract No. 1 dose groups, this can be expected to also have the effect of suppressing accumulation of fat in the body.

On the basis of these results, *Acacia* Hot Water Extract No. 1 was shown to reduce body fat.

Test Example 3

Mutagenicity Test

A mutagenicity test was conducted in compliance with Ministry of Health, Labor and Welfare Notification No. 77 (Sep. 1, 1988). As a result of testing with test substance (*Acacia* Hot Water Extracts Nos. 1 to 5 of Production Example 2) at doses of 156 to 5,000 μg/plate, there were no increases in the numbers of revertant colonies for any of the bacterial strains.

Test Example 4

Micronucleus Test

The presence of the ability to induce micronuclei was investigated in vivo in accordance with ordinary methods. *Acacia* Hot Water Extract No. 1 was orally administered twice at 24-hour intervals at daily doses of 2,000, 1,000 and 500 mg/kg to male ICR mice followed by the preparation of micronucleus specimens 24 hours after the final dosing. *Acacia* Hot Water Extract No. 1 did not demonstrate positive results at any of the dose levels. In addition, there were no constant fluctuations in the simultaneously observed ratio of total polychromatic erythrocytes to total erythrocytes, and inhibition of erythrocyte. proliferation was not observed in comparisons with a negative control group.

Test Example 5

Mouse Acute Toxicity Study (Oral Administration)

An acute oral dose toxicity study was conducted using male and female ICR mice in compliance with OECD (Guidelines for the Testing of Chemicals, 401, 1987). As a result, the $LD_{50}$ value of *Acacia* Hot Water Extract No. 1 was 4,468 mg/kg among males and 3,594 mg/kg among females.

Similar results were obtained in the above study for *Acacia* Hot Water Extracts Nos. 2 to 5 of Production Example 2.

Test Example 6

Rat Repeated Dose Toxicity Study (Oral Administration)

A 13-week repeated dose toxicity study was conducted using rats in accordance with ordinary methods. Mixed feed containing 0.5, 1.5 and 5.0% of *Acacia* Hot Water Extract No. 1 was fed to male and female Slc:SD rats.

As a result, none of the rats died or demonstrated abnormalities in examinations, including general condition.

Test Example 7

Human Single Dose Study

Five healthy adult males age 32 to 43 years were given 1500 mg of *Acacia* Hot Water Extract No. 1 (12 tablets of Formulation Example 4 described below). Although general examinations, hematology tests, blood biochemistry tests and urinalyses were performed on the subjects before ingestion, 3 hours after ingestion, 8 hours after ingestion, 24 hours after ingestion and 1 week after ingestion, there were no clinically significant fluctuations in test values. There were also no adverse events attributable to the tablets.

Test Example 8

Human 4-Week Continuous Dosing Study

Twenty-five healthy adult males age 23 to 44 years were given *Acacia* Hot Water Extract No. 1 of Formulation Example 4 described below at 750 mg/day (6 tablets of Formulation Example 4) and 1000 mg/day (8 tablets of Formulation Example 4) for 4 weeks each.

General examinations, hematology tests and urinalyses were performed on the subjects of each group before ingestion, 2 weeks after ingestion, 4 weeks after ingestion and 2 weeks following completion of ingestion. There were no clinically significant fluctuations in test values. There were also no adverse events.

Formulation Example 1

Preparation of Internal Medication

An internal medication having the composition indicated below was prepared using the *acacia* bark Hot Water Extract Ethanol Fraction of Production Example 4,

| | |
|---|---|
| Extract fraction of Production Example 4 | 1.0 (wt %) |
| Lactose | 30.0 |
| Cornstarch | 60.0 |
| Crystalline cellulose | 8.0 |
| Polyvinyl pyrrolidone | 1.0 |
| Total | 100.0 |

Formulation Example 2

Preparation of Pet Food

A pet food having the composition indicated below was prepared using the *acacia* bark Hot Water Extract of Production Example 2,

| | |
|---|---|
| Extract of Production Example 2 | 1.0 (wt %) |
| Oatmeal | 88.0 |
| Starch | 5.0 |
| Salt | 2.5 |
| Whole egg | 3.0 |
| Flavoring | 0.5 |
| Total | 100.0 |

Formulation Example 3

Preparation of Tablets (Confections)

Tablets (confections) having the composition indicated below were prepared using the *acacia* bark Hot Water Extract Ethanol Fraction of Production Example 4,

| | |
|---|---|
| Extract fraction of Production Example 4 | 1.0 (wt %) |
| Citric acid | 1.0 |
| Powdered skim milk | 15.0 |
| Sucrose ester | 1.0 |
| Flavoring | 0.5 |
| Powdered sugar | 20.0 |
| Lactose | 61.5 |
| Total | 100.0 |

Formulation Example 4

Preparation of Tablets

Tablets having the composition indicated below were prepared using *Acacia* Bark Hot Water Extract No. 1 of Production Example 2,

| | |
|---|---|
| Acacia Bark Hot Water Extract No. 1 of Production Example 2 | 125 (mg) |
| Sucrose ester | 9 |
| Lactose | 166 |
| Total | 300 |

INDUSTRIAL APPLICABILITY

The anti-obesity composition of the present invention is thought to be able to be used as a medicine or a food such as a health food, a health supplement food, a food for specified health use or a nutritional supplement food for use in preventing, decreasing and/or treating obesity. Moreover, it is also expected to be able to be used for the prevention and treatment of hypertension, diabetes, fatty liver, arteriosclerosis, stroke, hyperlipemia, peripheral circulatory disorders and ischeric heart disease.

The invention claimed is:

1. A method of suppressing the accumulation of body fat in a subject which comprises:
   administering to a subject in need thereof an anti-obesity composition comprising:
   (a) a hot water extract(s) of at least one *acacia* bark, wherein the *acacia* bark is obtained from at least one of *Acacia* mearnsii De Wild., *Acacia* mangium Willd., *Acacia* dealbata Link, *Acacia* decurrens Willd. and *Acacia* pycnantha Benth, and the hot water extract of *acacia* bark is a polyphenol;
   wherein the hot water extract(s) of *acacia* bark contains an *acacia* bark polyphenol(s), wherein the polyphenol(s) is a condensed tannin(s) having a molecular weight(s) of 500 to 3000, and is a polymer(s) of flavanols having flavan-3-ol as a basic skeleton linked by C4-C8 or C4-C6 bonds, and said flavan-3-ol is selected from the group consisting of (−)-fisetinidol, (−)-robinetinidol, (+)-catechin and (+)-gallocatechin,
   and at least one of vehicles, sweeteners, flavorings, thickeners, fragrances, pigments, emulsifiers, a food, a feed material, and a medicine; wherein the subject is a person or an animal with a high fat diet; and the composition contains an effective amount of the hot water extract of at least one *acacia* bark to suppress accumulation of body fat in the subject.

2. The method according to claim 1, wherein the *acacia* bark is a bark of *Acacia* mearnsii De Wild.

3. The method according to claim 1, wherein the *acacia* bark polyphenol(s) is orally ingested by the subject at 0.001 to 1 g per kg of body weight per day in terms of the amount of active ingredient.

4. The method according to claim 1, wherein the composition is in the form of a food, an animal feed material, or a medicine.

5. The method according to claim 1, wherein the effective amount of the hot water extract of at least one *acacia* bark is an amount of 0.001 to 1 g per kg of body weight per day in terms of the amount of active ingredient.

6. The method according to claim 5, wherein the effective amount of the hot water extract of at least one *acacia* bark is an amount of 0.001 to 0.5 g per kg of body weight per day in terms of the amount of active ingredient.

* * * * *